United States Patent [19]

Harvey

[11] Patent Number: 4,913,896

[45] Date of Patent: Apr. 3, 1990

[54] MULTI-PURPOSE BODY POWDER COMPOSITION

[76] Inventor: Norman A. Harvey, 19 Broad Acres Rd., Glens Falls, N.Y. 12801

[21] Appl. No.: 158,917

[22] Filed: Feb. 22, 1988

Related U.S. Application Data

[63] Continuation-in-part of Ser. No. 837,650, Mar. 5, 1986, abandoned, which is a continuation of Ser. No. 696,260, Jan. 30, 1985, abandoned.

[51] Int. Cl.$^4$ .............................................. A61K 7/035
[52] U.S. Cl. ...................... 424/69; 424/401; 514/560; 514/844; 514/865; 514/951
[58] Field of Search ............... 424/69, 401; 514/560, 514/844, 865, 951

[56] References Cited

U.S. PATENT DOCUMENTS 4,485,092  11/1984  Ashton et al. ..................... 424/69

FOREIGN PATENT DOCUMENTS 1357731  6/1974  United Kingdom ............... 514/778

OTHER PUBLICATIONS

Barnett, in Cosmetics: Science and Technology, 2nd Ed. vol. 1 (1972) pp. 136–137, 152–155.
Swanbeck, cited in Chem. Abstracts, vol. 85: 148985a 1976.
Poore, cited in Chem. Abstracts, vol. 87: 122645f (1977).
Shiseido Co., Ltd., cited in Chem. Abstracts, vol. 98: 22087j (1983).
Tukamoto et al, cited in Chem. Abstracts, vol. 80: 87415n (1974).

*Primary Examiner*—Jacqueline Stone
*Attorney, Agent, or Firm*—Schmeiser, Morelle & Watts

[57] ABSTRACT

A talc-base body powder composition having an unique composition of desirable characteristics including moisture absorbency, anti-ammonia, anti-bacterial and anti-fungal effects making it specially useful for infant skin care purposes consisting essentially of talc, cornstarch, calcium undeclyenate and citric or ascorbic acid in critical proportions.

5 Claims, No Drawings

MULTI-PURPOSE BODY POWDER COMPOSITION

This is a Continuation-in-Part of my copending patent application, Ser. No. 06/837,650, filed Mar. 5, 1986, now abandoned, which is a continuation of my patent application Ser. No. 696,260, filed Jan. 30, 1985, now abandoned.

FIELD OF THE INVENTION

The present invention relates generally to talc powder compositions for use in human skin scare, and is more particularly concerned with a novel multi-ingredient powder having a unique combination of desirable properties including moisture absorbency anti-ammonia, anti-bacterial and anti-fungal effects, making it especially useful for infant skin care purposes.

BACKGROUND OF THE INVENTION

In the field of human skin care, talc, which is a natural hydrous magnesium silicate, is the most important ingredient in most body powders. The excellent slip characteristics of a cosmetic grade of platelet talc provides a lubricant action between touching skin surfaces such as in the groin, axilla, neck and buttocks.

However, because pure talc powder does not absorb moisture well, many have employed powders consisting chiefly of starch and fragrance, with 0.05 methylbenzonium chloride often added for antiseptic action.

The starches do not slip or disperse as readily as talc but they have an excellent moisture absorbent quality. They are soft, white, odorless, nontoxic materials of small particle size, rice starch granules having an average diameter of 3 to $8\mu$ and cornstarch granules about $15\mu$.

The principal defect of starch is that it combines avidly with moisture and thus tends to become pasty, collecting in the groin and other folds, where it produces irritation. In addition, moist starch is an excellent culture medium for C. ALBICANS, a yeast-like fungus responsible for a severe form of diaper dermatitis in infants. For these reasons, Pediatric Dermatologists do not recommend pure cornstarch as a baby powder.

Attempts have been made to modify the starch granules both to decrease as well as to increase moisture absorbency. In order to decrease moisture absorbency, a chemically modified cornstarch known as Dry-Flo has been used. This is an aluminum salt of a low-substituted alkenyl succinic half-ester of starch. In order to increase the moisture absorbency of starch, others have used a pregelatinized starch. (U.S. Pat. No. 4,485,092).

Acid buffers have also been used in baby powders to counteract the alkalinity of talc, which in the unbuffered state has a pH of 9.0 to 9.3, considered by some as too alkaline for a baby's skin. Boric acid in 5% strength has long been used for this purpose and appears to help keep the pH of diaper just on the acid side of neutral. However, because of the toxicity of boric acid in more concentrated forms, Pediatric Dermatologists prefer that it not be used at all in baby skin powder preparations.

While non-toxic organic acids have been added to talc powder and to other skin care products, they have all been used in ways not related to use in accordance with the present invention. Thus, Tukamoto et al (Chem. Abstracts, Vol. 80, 87415, 1974) studied the stability of ascorbate salts in talc preparations, concluding that the calcium salt was most stable, next to that of the free acid, at the conditions specified. Also, 20% citric acid has been used to bind a polymer to talc powder to improve perfume retaining properties and heat stability. (Japanese Patent No. 57,145-007-1982). Still another publication (German patent No. 2,600,498) describes an aqueous solution of 0.5–3.0% NaCl in 0.2–1.0% lactic acid, thickened with carboxymethylcellulose for use in moistened wipes to clean the ano-genital areas of babies.

Another German patent No. (2,703,642) describes the addition of organic acids to body deodorants as a means of preventing bacterial decomposition of sweat, thus enchancing deodorant action.

The use of a buffer system is disclosed in British Patent No. 1,357,731 issued in 1970 to Lake who claimed success in maintaining a pH of 6.5 in the presence of 0.065N ammonia. The drawbacks to this approach include the fact that the buffer system alone accounts for 45% by weight of the finished powder composition, thus severely compromising the virtues of the inert ingredients (a) starch (added for softness and moisture absorption qualities) and (b) talc (necessary for its excellent slippage and lubricant qualities.) Moreover, this method requires the addition of an antibacterial agent such as BACTERIOSTAT or hexachloraphene, something obviated in the present invention.

Calcium undecylenate is an antifungal agent which also serves as a hydrophobic lubricant and water repellent. In the presence of moisture, this salt releases free undecylenic acid which is both antifungal and antibacterial.

The strengths of undecylenate used in powders at present varies from 20% in a popular foot powder, to 10% in one commercial baby powder. For the purpose of this invention, 3–6% calcium undecylenate is preferable.

The perfumes useful in this invention are any commercial perfume which results in a fragrance desired by the make of this powder composition.

Among the perfume components used in commercial perfume mixtures are: oil of lemon, cananga, sandalwood, copaiba, orange, nutmeg, geranium and lavender; as well as methyl gamma ionone, hydroxycitronellal, benzyl isoeugenol, musk ketone, ylang ylang oil, hexylcinnamic aldehyde, tetrahydro linalool, resin balsam fir, to name only a few.

The proper strength of fragrance is well known to those skilled in the art, and in powder preparations designed especially for babies, the least amount of fragrance necessary is generally used. According to Barnett, the fragrance in baby powder should be present in the 0.20%–0.25% range.

SUMMARY OF THE INVENTION

The overall objective of this invention is to provide a talc-base body powder composition Which is superior for skin care purposes to any such composition heretofore known.

A specific object of this invention is to provide a talc powder composition that has superior moisture absorbency over that of pure talc.

Another specific object of this invention is to provide a talc powder composition that possesses an anti-bacterial action.

Still another specific object of this invention is to provide a talc powder composition that possesses an antifungal action.

An additional specific object of this invention is to provide a talc powder composition that possesses an anti-ammonia effect, or ammonia neutralizing action.

Another important objective of this invention is to provide an unique product meeting all these requirements at cost comparable to that of the best commercially available talc-base body powders.

These and other objectives which will be apparent from the detailed description set out below have been achieved by this invention.

Underlying this invention is my novel concept that a powder composition having all the major characteristics to the desired extent might somehow be possible. This invention is also based upon my discovery that this new result can be obtained without using any substance which is either toxic or irritating to the skin of infants. It is also predicated upon my discovery that the porportions of the several constituents of my new powder compositions are important or ciritical to consistent success in reaching the goals of this invention.

More specifically, I have found that there are four essential ingredients and one optional ingredient (fragrance) and that partial, but quite limited, substitutions can be made for the talc and starch—two of the essential substances—without adversely affecting the desirable properties of these new powder compositions. Further, I have found that the proportion of talc should fall in the range of 65-80% while the starch should comprise from 20-30% of the powder composition and that the other two essentials, calcium undecylenate and citric acid or ascorbic acid, should be in amount from 2-10% and 0.25-2%, respectively. No more than 0.20 to 0.25% of fragrance is required for its special, but optional, purpose.

By using a cosmetic grade talc powder, and starch of the corn or rice variety of granule size from 3-8 micron size or about 15 micron size, respectively, in the above proportions, the moisture absorbency of the starch is fully exploited without tendency toward caking, stickiness, or loss of lubricity of the composition. In fact, the minor proportion of starch (about 20%) increases the fluid absorbency of the talc by a factor of about 46.5. Further, in these new products of this invention, the calcium undecylenate manifests a marked anti-bacterial effect in addition to its known anti-fungal effect. Finally, the acid constituent (ascorbic or citric) although in relatively small proportions, acts synergistically with the calcium undecylenate as an anti-bacterial agent, and also these two ingredients co-act to limit growth of bacteria which causes ammonia formation in the diaper area by releasing the enzyme, urease, by the reaction.

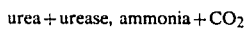

urea + urease, ammonia + $CO_2$

Thus, the direct anti-ammonia effect of organic acid is aided and supplemented by combined, synergistic, antibacterial effect of these two active agents, organic acid plus calcium undecylenate, limiting and discouraging the growth bacteria which causes ammonia formation in the first place.

When a powder composition is so made in accordance with this invention, it consequently possesses an unique combination of superior properties as stated above. Thus, the present invention generally described in composition of matter terms is a body powder composition consisting essentially of 65-80% talc, 15-22% starch, 2-10% calcium undecylenate, 0.25-2% citric or ascorbic acid, and optionally, 0.20-0.25% fragrance.

DETAILED DESCRIPTION OF THE INVENTION

The talc-base body powder composition of this invention may vary in formulation or proportion of the specific ingredients as indicated above, but they will all, nevertheless, share the same unique combination of desirable characteristics described above. In accordance with my present preference, relatively small amuonts of certain additives may be incorporated in these compositions for specific purposes, being substituted to the limited degree indicated below for the major constitutents, that is, the talc and the starch. Thus, the water repellent properties of the composition are improved by the addition of 3-5% of zinc, magnesium or lithium stearate, while the adherence and special properties such as astringency and deodorization are improved through incorporation of 2-5% of zinc oxide in the composition. Up to 5% kaolin improves the adherence, slippage and moisture absorptionand its high density reduces powder bulkiness. Finally, 1-3% of olive oil improves the emollience and adherence of the powder composition. These several additives may be incorporated, as those skilled in the art will understand, so that the ultimate powder compositin retains all its basic desirable properties in the unique combination described above and in essentially undiminished effect. Further, the ultimate composition in all cases will have the prescribed pH of this invention between 4.5 and 5.5.

It will be understood by those skilled in the art that the talc useful in accordance with this invention is a superior cosmetic grade of domestic or imported platelet talc, having particle size range from 15 to 40 microns, and which consequently passes through a 325 mesh screen to the extent of about 98%. Similarly, the cornstarch or rice starch useful is a pure cosmetic grade of unmodified starch with granules having average particle size of about 15 microns or in the case of rice starch, an average particle size of 3 to 8 microns.

The calcium undecylenate used in accordance with this invention is commercially available in the form of a dry light powder which is especially amenable to mixing with the other ingredients in these new compositions. The citric or ascorbic acid is likewise available commercially in pure form as powder material and is consequently also readily compounded in the production of these new compositions.

The fragrance of choice may be any single essence or combination of essences which will be compatible chemically and physically with the other constituents of the powder composition. Examples of such materials are oil of lemon, cananga, sandalwood, copaiba, orange, nutmeg, geranium, lavender, musk ketone, ylang ylang oil, resin balsam fir, hexylcinnamic aldehyde, tetrahydro linalool and hydroxycitronellal. The proportion of fragrance is noncritical and thus a matter of choice, it being recognized that the least amount of fragrance is generally used in body powder to be applied to the skin of infants.

The amounts of talc and starch as the major ingredients is fixed in the general ranges stated above and set out in the appended claims in accordance with my discovery, that unless the skin constituents are so proportined, the starch will tend to paste formation and collection in creases in skin where it will produce irritating effects. In addition, moist starch is an excellent culture medium for C. ALBICANS, a yeast-like fungus which causes a severe form of diaper dermatitis. For these reasons, pure cornstarch or rice starch is unsuitable as baby powder. On the other hand, talc should not be used in larger proportions than the maximum stated above because the powder would not then be capable of moisture absorption to the extent necessary to provide protection against wetness and irritation of the skin. Thus, in accordance with this invention, the present preferred composition affords the special merits and advantages of both the talc and the starch constituents as the moisture absorbency of the latter is twenty times greater than the talc, so that the mixture has the optimum measure of this important property.

In preparing the novel powder compositions of this invention, the talc, starch, calcium undecylenate and citric or ascorbic acid are mixed together thoroughly and blended in a commercial blender, and the fragrance is added through a liquid addition bar. The entire compositin is then mixed for five minutes, or so, followed by tumbling for fifteen minutes. The additional optional ingredients which may be used in partial substitution for the talc or starch constituents, or both of them, as detailed above and set out in the appended claims are incorporated in the mixture preferably prior to the addition of the fragrance. The blending and tumbling mixing operations being carried out as indicated above or in any other desired manner producing the substantial uniformity of mixture preferred in the best practice of this invention.

Those skilled in the art will gain a further and better understanding of this invention from the following illustrative, but not limiting, examples of the actual practice of this invention.

EXAMPLE I

A substantially uniform mixture of talc, cornstarch, calcium undecylenate and citric acid was prepared using a Mettler Electronic Balance, Model AC100, accurate to 0.001 gram. The talc powder was USP quality, 76 grams being used. The cornstarch was likewise in powder form, and USP quality, used in amount of 20 grams. The calcium undecylenate was also powder, a product of Albany Laboratories, Inc., 3 grams being used. The citric acid was a powder produced and marketed by Pharmaceutical Supply Co., the amount being 1 gram in this case. These constituents were mixed in Waring Blender for 5 minutes, followed by tumbling for 10 minutes. The volume of the individual constituents of the 100 gram mixture were as follows: talc - 78%, cornstarch - 14%, calcium undecylenate - 7%, citric acid - 1%. It is thus apparent that starch occupies a smaller percent volume while the calcium undecylenate occupies a considerably larger proportion of the volume then their respective weights would indicate.

This mixture of this invention was tested in several ways as detailed in the following examples.

EXAMPLE II

Using the test procedure described in Example II of U.S. Pat. No. 4,485,092, the powder formulation of Example I was tested for moisture absorbency against plain talc of the sort that was used in preparing the mixture. In this test, there was an increase in fluid absorbency from 0.02 ml per gram of plain talc to 0.93 ml per gram in the formulation of this inventino as prepared in Example I. Thus, there was an increase of 46.5 fold over the plain talc in respect to this important physical property.

EXAMPLE III

Again using the formulation of this invention as prepared according to Example I, the pH of the formulation was tested against that of plain talc. A Mettler AC100 scale was used to measure the weight of the powders, and the pH meter used was a Corning Digital 109, the diluent used being a 0.9% sodium chloride (IV solution) manufactured by Travenol Laboratories. In carrying out the experiment to a seven-gram aliquot of each powder, 14 ml of the saline solution of pH 6.8 was added and mixed to loose paste consistency. The test samples were allowed to stand for 5 mintues while the pH aliquot of each powder, 14 ml of the saline solution of pH 6.8 was added and mixed to loose paste consistency. The test samples were allowed to stand for 5 mintues while the pH meter was being calibrated. The pH of the formulation of this invention was found to be 5.2 while the pH of the plain talc was measured at 8.6.

EXAMPLE IV

An experiment was performed to test the anti-ammonia effect of the formulation of this invention. In this experiment, 5.0 ml of 1% ammonia solution of pH to 11.3 and a two gram aliquot of powder mixture of the formulation of Example I was added and shaken and mixed thoroughly. The pH of the mixture of ammonia and powder was then determined to be 9.8. the 1% ammonia solution (0.38 Normal) used in these studies is considerably stronger than the traces of ammonia found in infant diapers.

It follows from these results that the addition of citric or ascorbic acid in accordance with this invention (0.5 to 2.0%) accomplishes a direct ammonia neutralization effect with a minimal dilution of the starch and the talc which have in themselves highly desirable qualities. This contrasts with the prior art whrein as much as 45% by weight of body powder formulations is used for buffering purposes to accomplish the same neutralizing effect or neutrality. Such dilution and resulting compromise of those desired properties does not result in accordance with the applicant's invention.

EXAMPLE V

The formulation of this invention, prepared as described in Example I, was used in tests of intended purposes in application to the skin of babies in the usual manner with successive diaper changes. There was not evidence in any instance of caking of the powder on skin, nor was there any sign of irritation of the portions of the areas of infant's skin treated with this powder.

EXAMPLE VI

A substantially uniform mixture of talc, cornstarch and citric acid was prepared by blending powder mixer in the proportions of 67% talc, 31% cornstarch and 2% citric acid. The powders used were those presently available on the commercial market and the mixer was a standard device of the type. The resulting batch mixture amounting to about 500 grams was tested by applying it to a baby's skin in the usual manner with successive diaper changes. Ther was not evidence of caking of the powder on the skin nor was there any sign of irritation of the portions of the areas of the infant's skin treated with this powder.

EXAMPLE VII

Another batch of powder was prepared in the manner described in Example VI using calcium undecylenate powder in addition to the constituents specified therein. The proportions in this case were; about 72% talc, about 22% cornstarch, about 5% calcium undecylenate and about 1% citric acid. Testing of this powder product as described above yielded the same ultimate results.

In the specification and the appended claims whenever amounts, proportions or percentage are stated, reference is to the weight basis unless otherwise expressly noted.

The pH values stated herein and in the appended claims are those measured in conventional manner in the presence of moisture sufficient for ionization effect, as those skilled in the art will understand.

I claim:

1. A multi-purpose body powder composition having moisture absorbency at least 20 times greater than that of talc consisting essentially of about 65% to 80% of the total composition of talc, about 15% to 30% of the total composition of starch, about 2% to 10% of the total composition of calcium undecylenate, about 0.25% to 2% of the total composition of citric acid or ascorbic acid, and optionally, about 0.20% to 0.25% fragrance, said starch being of pure cosmetic grade unmodified granular starch selected from the group consisting of cornstarch of average particle size about 15 microns and rice starch of average particle size of 3 to 8 microns, and said powder composition having pH of 4.5 to 5.5.

2. The composition of claim 1 in which the talc content is 76%, the starch is cornstarch in the amount of 20%, the calcium undecylenate is 3% and acid is citric in amount of 1%.

3. The composition of claim 1 containing 2-5% zinc oxide, up to 5% kaolin, 1-3% olive oil, and 3-5% of zinc magnesium or lithium stearate.

4. The composition of claim 1 consisting essentially of 76% talc, 20% cornstarch, 3% calcium undecylenate, and 1% citric acid; said composition having pH of 5.2.

5. A baby skin care powder composition consisting essentially of about 72% talc, about 22% cornstarch, and about 5% calcium undecylenate and about 1% citric acid.

* * * * *